US012614257B2

(12) United States Patent
Jahren et al.

(10) Patent No.: US 12,614,257 B2
(45) Date of Patent: Apr. 28, 2026

(54) SYSTEMS AND METHODS FOR CLUTTER ARTIFACT REMOVAL USING A DATA-DRIVEN MODEL TRAINED ON IMAGES FORMED USING A LOWER CLUTTER IMAGE SEQUENCE AND A HIGHER CLUTTER IMAGE SEQUENCE GENERATED BY AN ARTIFACT OVERLAY ON THE LOWER CLUTTER IMAGE SEQUENCE

(71) Applicant: GE Precision Healthcare LLC, Wauwatosa, WI (US)

(72) Inventors: Tollef Jahren, Oslo (NO); Anders R. Sørnes, Oslo (NO); Bastien Denarie, Oslo (NO)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 419 days.

(21) Appl. No.: 18/186,809

(22) Filed: Mar. 20, 2023

(65) Prior Publication Data

US 2024/0320801 A1     Sep. 26, 2024

(51) Int. Cl.
*G06N 3/0464* (2023.01)
*G06T 5/70* (2024.01)
(Continued)

(52) U.S. Cl.
CPC .............. *G06T 5/70* (2024.01); *G06T 7/0012* (2013.01); *G16H 30/40* (2018.01);
(Continued)

(58) Field of Classification Search
CPC . G06T 2207/10016; G06T 2207/10132; G06T 2207/20081; G06T 2207/20084;
(Continued)

(56) References Cited

U.S. PATENT DOCUMENTS

2020/0126190 A1* 4/2020 Lebel ........................ G06T 5/60
2021/0295474 A1* 9/2021 Wang ..................... G06N 3/084
2024/0233091 A9* 7/2024 Huber ...................... G06T 5/60

OTHER PUBLICATIONS

Brickson et al. "Reverberation Noise Suppression in Ultrasound Channel Signals Using a 3D Fully Convolutional Neural Network". Pertinent pp. 1-12. (Year: 2020).*
(Continued)

*Primary Examiner* — Chad Dickerson
(74) *Attorney, Agent, or Firm* — McCoy Russell LLP

(57) ABSTRACT

The current disclosure provides systems and methods for reducing clutter artifacts in medical images. In one example, a method for an image processing system comprises receiving a sequence of medical images including an amount of clutter artifacts; reducing the amount of clutter artifacts present in the sequence of medical images using a trained data-driven model, the data-driven trained on image sequence pairs including a first, lower-clutter image sequence as a target image, and a second, higher-clutter image sequence as an input image, the higher-clutter image sequence generated by superimposing an artifact overlay on the lower-clutter image sequence, the lower-clutter image sequence generated by an imaging device during a medical exam of a subject; and displaying an artifact-reduced version of the sequence of medical images on a display device of the image processing system, the artifact-reduced version outputted by the data-driven model.

18 Claims, 10 Drawing Sheets

(51) Int. Cl.
　　*G06T 7/00*　　　　(2017.01)
　　*G16H 30/40*　　　 (2018.01)
　　*G06T 5/00*　　　　(2024.01)

(52) U.S. Cl.
　　CPC ............... *G06T 2207/10016* (2013.01); *G06T 2207/10132* (2013.01); *G06T 2207/20081* (2013.01); *G06T 2207/20084* (2013.01); *G06T 2207/20212* (2013.01); *G06T 2207/30048* (2013.01); *G06T 2207/30168* (2013.01)

(58) Field of Classification Search
　　CPC . G06T 2207/20212; G06T 2207/30048; G06T 2207/30168; G06T 5/60; G06T 5/70; G06T 7/0012; G16H 30/40
　　USPC ......................................................... 382/128
　　See application file for complete search history.

(56) References Cited

OTHER PUBLICATIONS

Tabassian et al. "Clutter Filtering Using a 3D Deep Convolutional Neural Network". Pertinent pp. 1-4. (Year: 2019).*

Mauldin, F. et al., "The Singular Value Filter: A General Filter Design Strategy for PCA-Based Signal Separation in Medical Ultrasound Imaging," IEEE Transactions on Medical Imaging, vol. 30, No. 11, Nov. 2011, 35 pages.

Tabassian, M. et al., "Clutter Filtering Using a 3D Deep Convolutional Neural Network," Proceedings of the 2019 IEEE International Ultrasonics Symposium (IUS), Oct. 6, 2019, Glasgow, UK, 4 pages.

Sjoerdsma, M. et al., "A Spatial Near-Field Clutter Reduction Filter Preserving Tissue Speckle in Echocardiography," IEEE Transactions on Ultrasonics, Ferroelectrics, and Frequency Control, vol. 68, No. 4, Apr. 2021, Available Online Mar. 26, 2021, 14 pages.

Brickson, L. et al., "Reverberation Noise Suppression in Ultrasound Channel Signals Using a 3D Fully Convolutional Neural Network," IEEE Transactions on Medical Imaging, vol. 40, No. 4, Apr. 2021, Available Online Apr. 1, 2021, 12 pages.

* cited by examiner

SYSTEMS AND METHODS FOR CLUTTER ARTIFACT REMOVAL USING A DATA-DRIVEN MODEL TRAINED ON IMAGES FORMED USING A LOWER CLUTTER IMAGE SEQUENCE AND A HIGHER CLUTTER IMAGE SEQUENCE GENERATED BY AN ARTIFACT OVERLAY ON THE LOWER CLUTTER IMAGE SEQUENCE

TECHNICAL FIELD

Embodiments of the subject matter disclosed herein relate to medical imaging, and more particularly, to systems and methods for removing noise from medical images.

BACKGROUND

Medical images may include an amount of noise, which may reduce a quality of the medical images and hinder diagnosis. One type of noise not untypical in ultrasound imaging, in particular, trans-thoracic cardiac imaging, includes artifacts that may be referred to as clutter, haze, or reverberations. These artifacts originate from undesired acoustic interaction with lung or other untargeted tissues via ribs or other hard structures of a subject. Clutter artifacts can obscure diagnostic information from an examiner, and may be a frequent reason for patients having to be referred to more invasive, unpleasant or expensive examinations, such as Trans-esophageal (TEE) ultrasound, contrast, or other imaging modalities. Removing these artifacts may increase the diagnostic potential of ultrasound imaging in a wider population of patients, reduce a probability of misdiagnosis, and reduce a cost and a time of examination.

One approach to removing this type of artifact is based on wavelet decomposition. However, such methods may rely on spatial information, and may discard temporal information. Other approaches employ temporal filtering to reduce the clutter contents, but may not account for its spatial properties. Clutter artifacts could be more efficiently identified and removed if both spatial and temporal information were utilized, because target structures tend to move coherently in one cohesive motion, while the haze forms a pattern abiding a different trajectory. Thus, clutter artifact reduction may be facilitated by separating signals based on a relative motion of spatial patterns.

SUMMARY

The current disclosure at least partially addresses one or more of the above identified issues by a method for an image processing system, comprising receiving a sequence of medical images including an amount of clutter artifacts; reducing the amount of clutter artifacts present in the sequence of medical images using a trained data-driven model, the data-driven model trained on image sequence pairs including a first, lower-clutter image sequence as a target image, and a second, higher-clutter image sequence as an input image, the higher-clutter image sequence generated by superimposing an artifact overlay on the lower-clutter image sequence, the lower-clutter image sequence generated by an imaging device during a medical exam of a subject; and displaying an artifact-reduced version of the sequence of medical images on a display device of the image processing system and/or storing the artifact-reduced version in a memory of the image processing system, the artifact-reduced version outputted by the data-driven model.

In various embodiments, the medical images may be ultrasound images acquired via an ultrasound probe during a transthoracic cardiac imaging examination. The artifact overlay sequence for each lower-clutter image sequence may be created from patches of haze extracted from a similar higher-clutter image sequence, where the patches may be taken from areas of the higher-clutter image sequence not including anatomical features or structures of a scanned region of interest (e.g., a cavity). The patches may be combined, tiled, and/or augmented to create a haze overlay (e.g., artifact overlay) with a same set of dimensions as the lower-clutter image sequence, such that when superimposed on the lower-clutter image sequence, a version of the lower-clutter image sequence is generated with a greater amount of haze or clutter artifacts. The lower-clutter image sequence and the version of the lower-clutter image sequence with added clutter may then be paired as a training pair, to be used to train the data-driven model. The data-driven model may be a neural network model, or a statistical model, or a different type of trainable model.

An advantage of the artifact overlay described herein over other approaches, such as simulating artificial noise, is that using an overlay generated from patches of haze taken from ultrasound images may ensure that realistic clutter artifact data is added to the lower-clutter image sequence. Artificially creating noise with the same properties as haze may not be straightforward. For example, random or semi-random noise within a frequency band may not be representative of haze. Clutter artifacts could be added via an acoustic wave simulation, but as the mechanisms for clutter formulation and dynamics are diverse and complex, setting up an acoustic wave simulation to capture a variety of types of haze may be unfeasible or difficult.

An additional advantage of the methods described herein is that the data-driven model may use a temporal evolution of an ultrasound image over time to distinguish structural elements of an ultrasound image from haze. The structural elements may be distinguished based on a difference between a collective motion of the structural elements versus a relative motion of the pattern of haze over a sequence of images. A temporal consistency between the lower-clutter images and the higher-clutter images used to generate the overlay may be maintained by the fact that the clutter is to some extent moving independently of the heart, and is indirectly affected by heart events intermittently when pulse events shake surrounding tissues. Since the structural information in the low- and higher-clutter images is the same, and the difference is the higher-clutter overlay which is expected to move largely differently than the structure, the training sequences may remain consistent for each frame in a succession of frames. The use of the same low clutter image sequence as the structural underlay in the higher clutter sequence may also ensure that the temporal consistency is also maintained between the images of the training sequence pair. Alternatively, the temporal consistency of the artifact overlays and the higher-clutter image sequences with respect to the lower-clutter image sequences may be maintained by careful use of simultaneously acquired ECG trace data or other cardiac event data for synchronization. In various embodiments, the data-driven model may be a spatio-temporal convolutional neural network (CNN), where a plurality of training pairs of images of an acquired sequence of images are inputted into the CNN at each iteration, thus providing the CNN with the temporal information to distinguish the haze from the structural elements.

It should be noted that while the systems and methods disclosed herein are described in reference to transthoracic echocardiograms (TTE), the systems and methods can be generalized to other types of probes (e.g., transesophageal echocardiography (TEE) probes) and/or ultrasound applications prone to reverberation artifacts. The systems and methods may also apply to other types of medical imaging, such as computed tomography (CT), magnetic resonance imaging (MRI), or a different type of medical imaging.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

Figure 1:
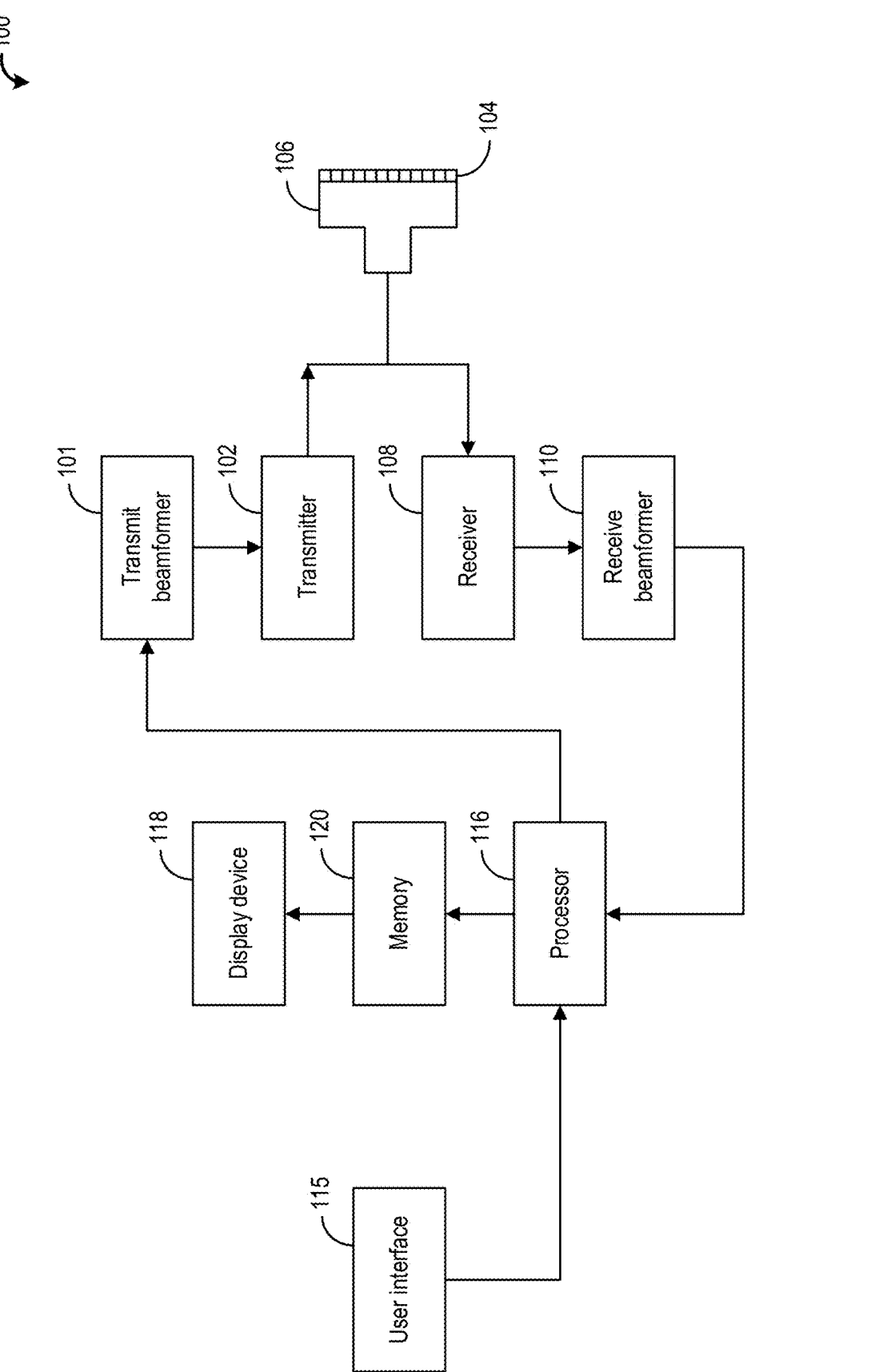
FIG. 1 shows a block diagram of an exemplary embodiment of an ultrasound system.

The drawings illustrate specific aspects of the described systems and methods for removing clutter artifacts from ultrasound images. Together with the following description, the drawings demonstrate and explain the structures, methods, and principles described herein. In the drawings, the size of components may be exaggerated or otherwise modified for clarity. Well-known structures, materials, or operations are not shown or described in detail to avoid obscuring aspects of the described components, systems, and methods.

DETAILED DESCRIPTION

Systems and methods are disclosed for removing acoustic noise originating from undesired acoustic interaction with lung or other untargeted tissues via the ribs or other hard structures from live cardiac ultrasound images. The removal of the acoustic noise (e.g., clutter) is achieved by using a data driven, supervised model, such as a spatio-temporal convolutional neural network (CNN). The model may be trained on training data generated as described herein. Specifically, the model can be trained to separate superimposed moving clutter from clutter-free 2D cardiac image sequences using a large collection of clinical data.

A set of clinical image sequences (1D, 2D, or 3D plus time) can be categorized into a first set of sequences exhibiting insignificant amounts of clutter, and a second set of sequences exhibiting excessive amounts of clutter. The clinical images may include in-vivo imaging data from any stage of an image acquisition chain of an imaging system, where the image acquisition chain spans from a generation of a signal, to displaying an image on a display device of an imaging system. In one example described herein, the imaging data is echography ultrasound data from an ultrasound imaging system.

From the second, excessively cluttered datasets, clutter residing in hypo-echoic regions of corresponding images may be extracted from adjacent cardiac structures, stacked, and augmented to form realistic clutter overlays devoid of any structural information. These clutter-overlays may then be superimposed onto the first set of relatively clutter-free clinical raw data time sequences. In this way, a collection of hazy clinical ultrasound data can be generated for which lower-clutter ground-truth sequences are known (harvested off the clutter-free category). These two sets of data may then be used to supervise the training of the data-driven model. The ultrasound data on which the data driven model is trained can be in various forms, such as radio frequency (RF) data, complex demodulated in-phase and quadrature (IQ) channel data, envelope data or log-compressed envelope data, pre-beamformed, beamformed IQ data, or scan converted data. The way ultrasound data is traditionally recorded, by scanning through a set of beams at different angles, the data naturally exists first in a beamspace format and has to be scan converted in order for the displayed data to match a real geometry of the object. In various embodiments, the ultrasound data on which the data driven model is trained may be linear domain amplitude beamformed IQ (complex) data in beamspace, where raw data acquired via an ultrasound probe in a scan is arranged in a rectangular shape, where beam data is represented vertically and the horizontal axis is scan angle or beam index.

Beamformed ultrasound data exists first as in-phase/quadrature (IQ) data made up of complex numbers with both a phase and an amplitude. IQ demodulation may be used to save bandwidth, and may be equivalent to RF data if the phase is tracked during envelope detection. Prior to detection, underlying structural image data may be separated from clutter due to a linearity of image data in this format. Before display (and before log compression), the IQ data used for training the data-driven model may be envelope detected, where the absolute value of the complex number is used, disregarding the phase information. It may be more difficult to separate clutter from structural underlay in envelope data, both since the phase information is lost, and because the assumption that the resultant signal is an addition may not be strictly valid.

Alternatively, the data used for training the data-driven model may be in a logarithmic domain, for example, if amplitudes of the raw image data have been log compressed for mapping to grayscale values for display on a screen. With log compressed data, it may be easier to detect both weaker and stronger amplitudes at the same time (as the dynamic range is reduced) than in the linear domain, where weak structures may be less significantly represented and hence difficult to 'see'.

The data used for training the data-driven model may also be scan converted data. Raw beamspace data is arranged as a series of beams, each beam including a series of samples, the data thus displaying like a rectangular image, although a direction of each beam corresponds to an angle (e.g., like a fan). When the beam space data is scan converted, a resulting image is remapped by interpolation into x,y,z coordinates that have a correct physical shape representing the imaged object, without distortion.

In some embodiments, the data used for training the data-driven model may be channel data, a rawest data format where individual receive signals from each transducer element have not yet been delayed and summed into a particular beam in a direction. In such cases, the raw image data using for training the data-driven model comprise signals in each channel for each transmit beam. Channel data may provide extra information to help the model separate clutter from a structural underlay. However, the identification and extraction of clutter may be more elaborate and less intuitive to execute.

Other approaches to removing clutter that rely on models for removing reverberation overlays from ultrasound image sequences have used simulated data for both the reverberations and the ultrasound image, such as simple geometric shapes with relatively low realism. However, clutter in cardiac ultrasound images originates from a variety of different, complex acoustic multi-scattering pathways that may be difficult to model or simulate correctly, and due to a lack of diversity of simulated data used in training, a performance of CNNs trained on such data may be limited. Additionally, a network's ability to remove clutter from real data may depend on capturing both an accurate representation of the reverberations and their time evolution in the training data.

As a result, a novel approach to training a neural network model to detect and remove reverberations from medical images is proposed herein, including generating training data based on real clinical images such as ultrasound images, and real reverberations, and inputting training data including image sequences to leverage information about how clutter moves in concert over time.

One or more ultrasound images may be acquired via an ultrasound probe of an ultrasound imaging system, such as the ultrasound imaging system of FIG. 1. The ultrasound imaging system may be communicatively coupled to an image processing system, such as the image processing system of FIG. 2. The image processing system may include one or more neural network models stored in non-transitory memory. An exemplary neural network algorithm may be trained using an artifact reduction network training system shown in FIG. 3A, to remove clutter artifacts from the ultrasound images. Training data for the artifact reduction network training system may be generated as shown in FIG. 3B. Haze data may be extracted from the higher-clutter ultrasound images, as shown in FIG. 4A. Extracted haze patches may be superimposed on a haze-free image sequence to generate training pairs of images for training the artifact reduction network, as shown in FIG. 4B. A data-driven model such as an artifact reduction network may be trained to remove clutter artifacts from the ultrasound images by following one or more steps of the method of FIG. 5, where the artifact reduction network may be trained on training data generated by following one or more steps of the method of FIG. 6. After the artifact reduction network has been trained, the trained artifact reduction network may be used to remove clutter artifacts from new ultrasound images by following one or more steps of the method of FIG. 7. An example of an ultrasound image with clutter artifacts removed is shown in FIG. 8.

Referring now to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). The probe 106 may be a one-dimensional transducer array probe, or the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient clinical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and/or a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications.

The processor 116 may control the probe 106 to acquire data according to instructions stored on a memory of the processor, and/or memory 120. The processor 116 may control which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain.

The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time frame-rate of 7-20 frames/sec. The ultrasound imaging system 100 may acquire 2D data of one or more planes at a significantly faster rate. However, it should be understood that the real-time frame-rate may be dependent on a length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec.

The data may be stored temporarily in a buffer (not shown) during a scanning session and processed in less than real-time in a live or off-line operation. In some embodiments, multiple processors (not shown) may be included to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present disclosure, data may be processed in different mode-related modules by the processor 116 (e.g., B-mode, Color Doppler, M-mode, Color M-mode, spectral Doppler, Elastography, TVI, strain, strain rate, and the like) to form spatio-temporal 2D, 3D, or 4D data (e.g., where time is included as one dimension). For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing an ultrasound scan, a two-dimensional block of data comprising scan lines and their samples is generated for each row of transducers comprised by the ultrasound probe (e.g., one block of data for a 1D probe, or n blocks of data for a 2D probe with n rows of transducers). After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (e.g., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Ultrasound data acquired by ultrasound imaging system 100 may be further processed at various stages before, during, or after image formation. In some embodiments, as described in greater detail below, ultrasound data produced by ultrasound imaging system 100 may be transmitted to an image processing system, where the ultrasound data may be processed by one or more data-driven models. For example, a neural network model may be trained using ultrasound images and corresponding ground truth images to increase a quality of the ultrasound images. As used herein, ground truth output refers to an expected or "correct" output based on a given input into a machine learning model. For example, if a machine learning model is being trained to reduce an amount of noise and/or artifacts in an ultrasound image, the ground truth output for the model, when fed an input image, may be an ultrasound image with a desired (low) amount of noise and/or artifacts.

Although described herein as separate systems, it will be appreciated that in some embodiments, ultrasound imaging system 100 includes an image processing system. In other embodiments, ultrasound imaging system 100 and the image processing system may comprise separate devices. In some embodiments, images produced by ultrasound imaging system 100 may be used as a training dataset for training one or more machine learning models, wherein the machine learning models may be used to perform one or more steps of ultrasound image processing, as described below.

Figure 2:
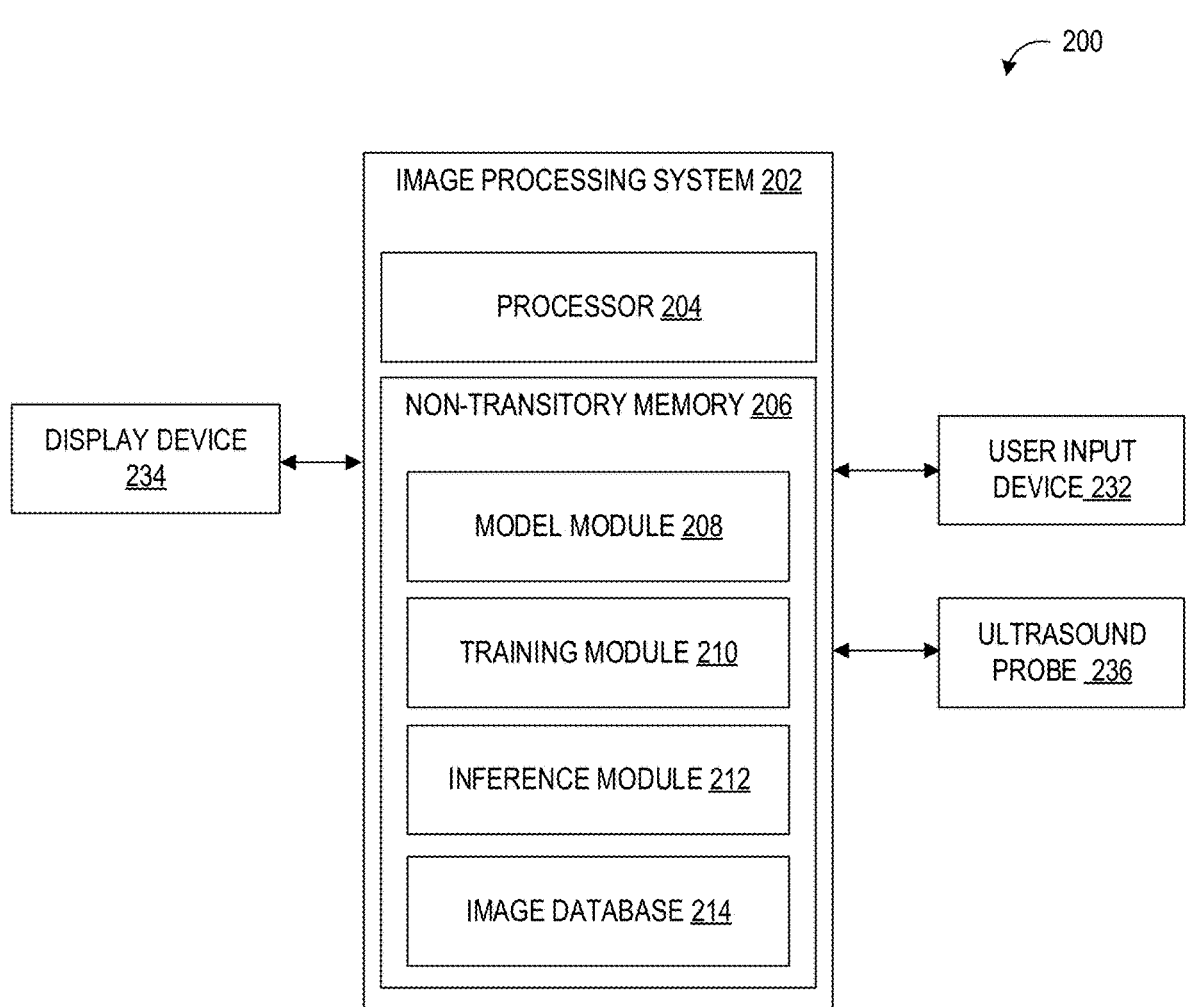
FIG. 2 shows a block diagram of an exemplary embodiment of an image processing system.

Referring to FIG. 2, a block diagram 200 shows an image processing system 202, in accordance with an embodiment. In some embodiments, image processing system 202 is incorporated into the ultrasound imaging system 100. For example, image processing system 202 may be provided in the ultrasound imaging system 100 as the processor 116 and memory 120. In some embodiments, at least a portion of image processing 202 is disposed at a device (e.g., edge device, server, etc.) communicably coupled to the ultrasound imaging system via wired and/or wireless connections. In some embodiments, at least a portion of image processing system 202 is disposed at a separate device (e.g., a workstation) which can receive images from the ultrasound imaging system or from a storage device which stores the images/data generated by the ultrasound imaging system. Image processing system 202 may be operably/communicatively coupled to a user input device 232 and a display device 234. User input device 232 may comprise the user interface 115 of the ultrasound imaging system 100, while display device 234 may comprise the display device 118 of the ultrasound imaging system 100, at least in some examples. Image processing system 202 may also be operably/communicatively coupled to an ultrasound probe 236.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, processor 204 may optionally include individual components that are distributed throughout two or more devices, which may be remotely located and/or configured for coordinated processing. In some embodiments, one or more aspects of processor 204 may be virtualized and executed by remotely-accessible networked computing devices configured in a cloud computing configuration.

Non-transitory memory 206 may store a model module 208, a training module 210, an inference module 212, and an image database 214. Model module 208 may include at least a data-driven model, and instructions for implementing the data-driven model to reduce an amount of artifacts in ultrasound images, as described in greater detail below. Model module 208 may include models of various types, including trained and/or untrained neural networks such as CNNs, statistical models, or other models, and may further include various data, or metadata pertaining to the one or more models stored therein.

Non-transitory memory 206 may further store a training module 210, which may comprise instructions for training one or more of the models stored in model module 208. Training module 210 may include instructions that, when executed by processor 204, cause image processing system 202 to conduct one or more of the steps of method 500 for training a neural network model, discussed in more detail below in reference to FIG. 5, and one or more of the steps of method 600 for generating a training dataset for training the neural network model, discussed in more detail below in reference to FIG. 6. In some embodiments, training module 210 may include instructions for implementing one or more gradient descent algorithms, applying one or more loss functions, and/or training routines, for use in adjusting parameters of one or more neural networks of model module 208. Training module 210 may include training datasets for the one or more models of model module 208.

Non-transitory memory 206 also stores an inference module 212. Inference module 212 may include instructions for deploying a trained data-driven model, for example, to reduce an amount of artifacts in ultrasound images as described below with respect to FIG. 7. In particular, inference module 212 may include instructions that, when executed by processor 204, cause image processing system 202 to conduct one or more of the steps of method 700, as described in further detail below.

Non-transitory memory 206 further stores image database 214. Image database 214 may include for example, ultrasound images acquired via an ultrasound probe. For example, image database 214 may store images acquired via a handheld ultrasound probe placed on a body of a subject, and/or images acquired via an endoscopic ultrasound probe inserted into a cavity of the body of the subject. Image database 214 may include ultrasound images used in one or more training sets for training the one or more neural networks of model module 208.

In some embodiments, non-transitory memory 206 may include components disposed at two or more devices, which may be remotely located and/or configured for coordinated processing. In some embodiments, one or more aspects of non-transitory memory 206 may include remotely-accessible networked storage devices configured in a cloud computing configuration.

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of an image to use in training a machine learning model, or for further processing using a trained machine learning model.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

Figure 3A:
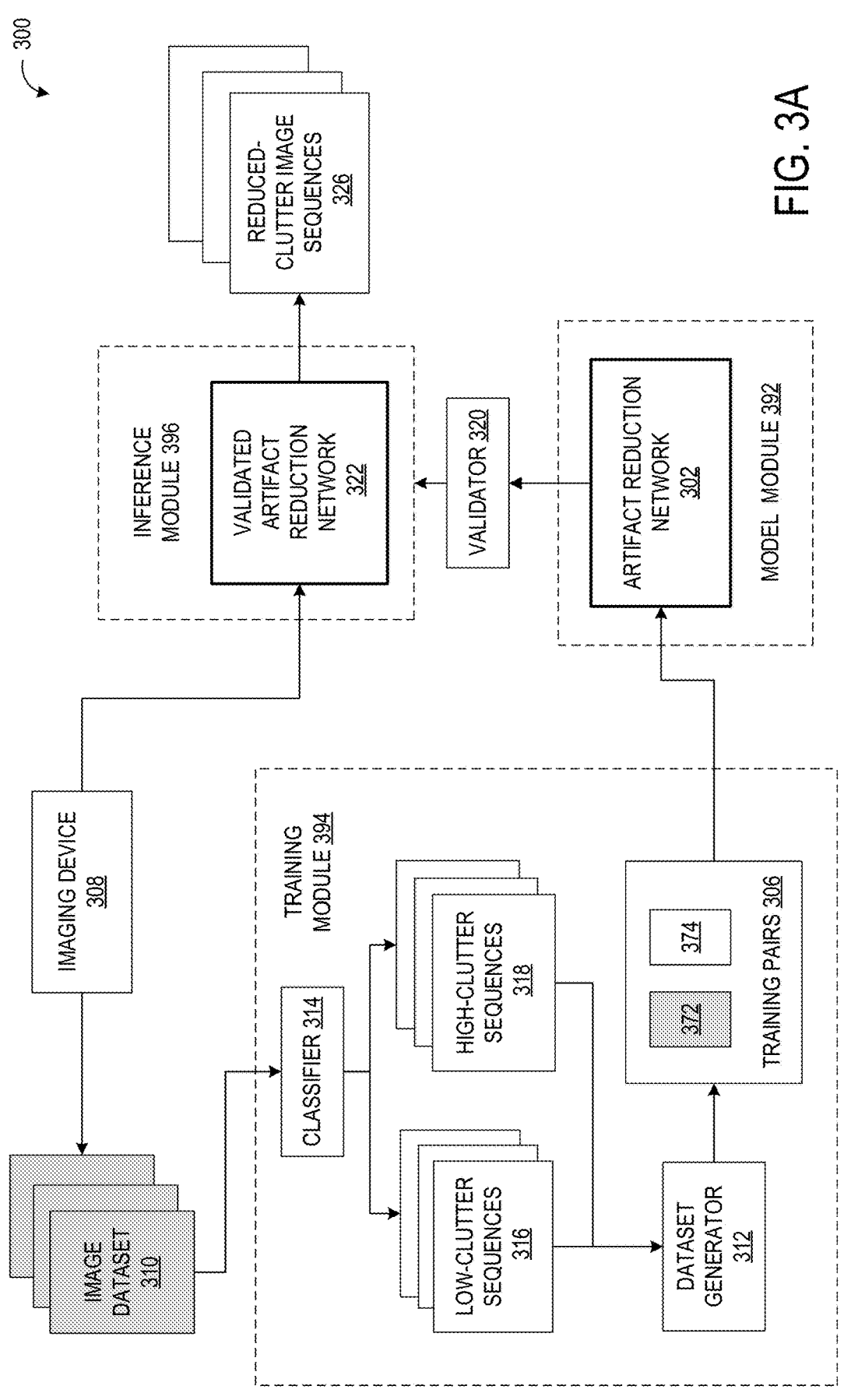
FIG. 3A shows a block diagram of an exemplary embodiment of an artifact reduction network training system.
Figure 3B:
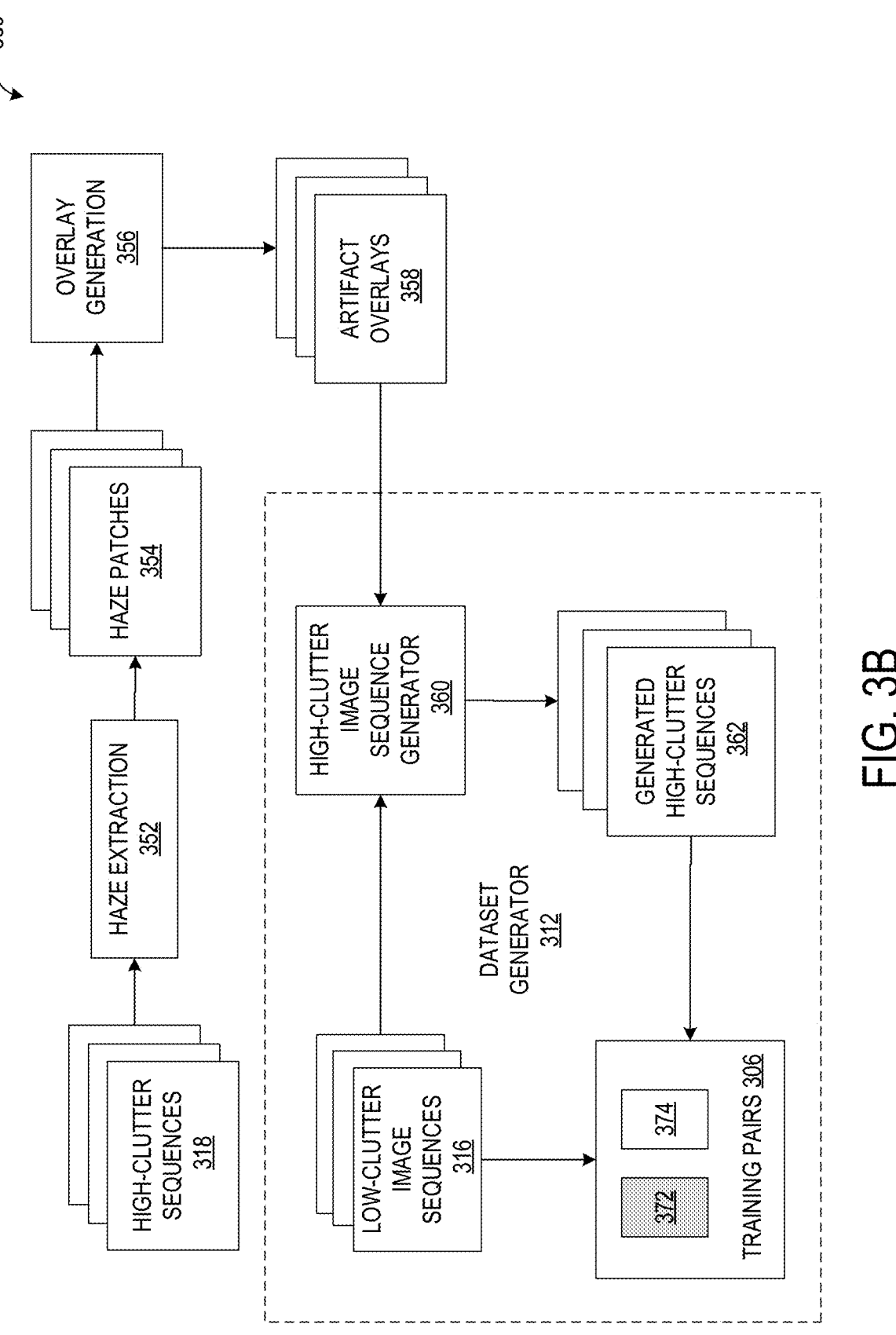
FIG. 3B shows a block diagram of an exemplary embodiment of a system for generating training data for the artifact reduction network training system.
Figure 4A:
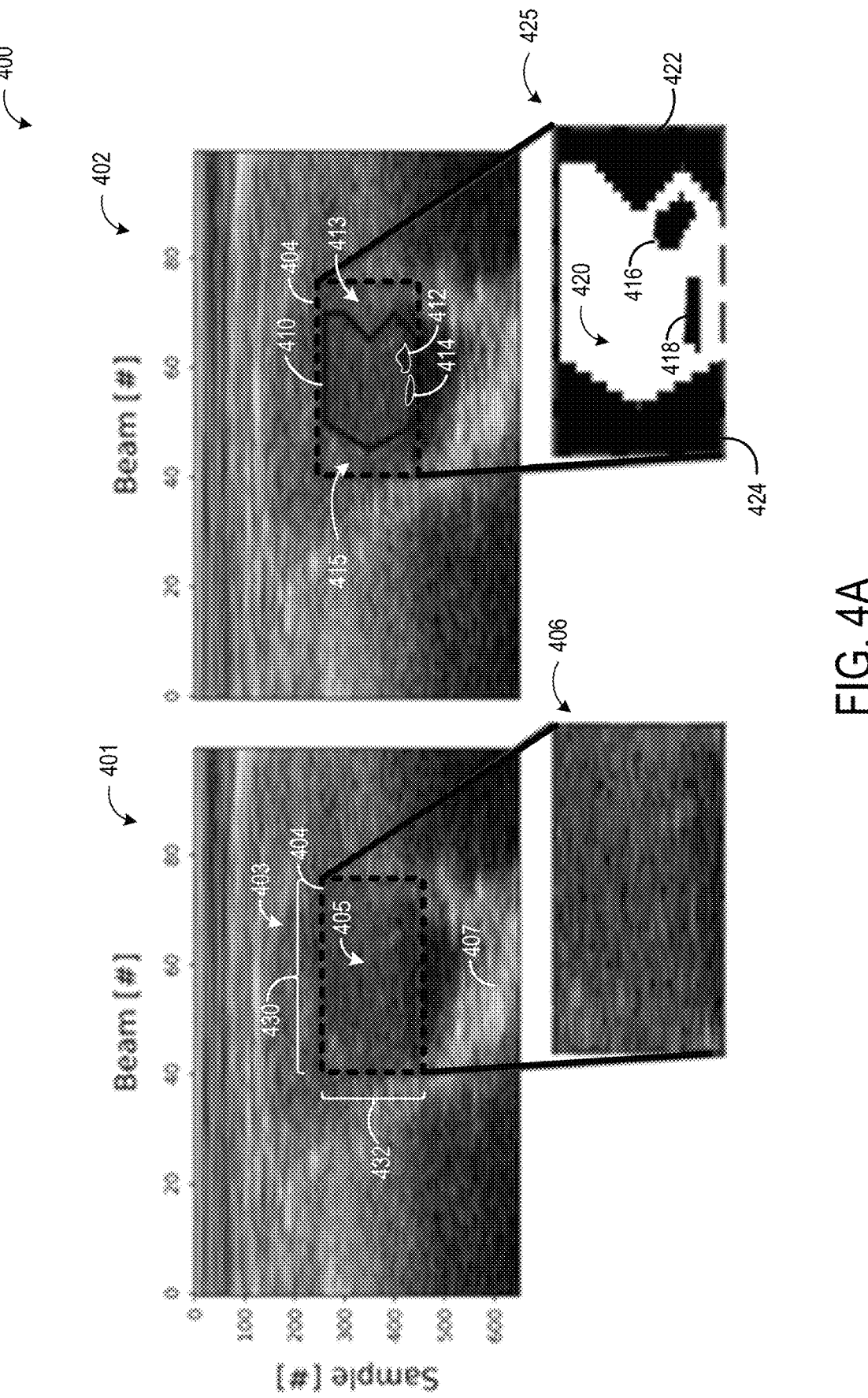
FIG. 4A shows an example of an extraction of a haze patch from a hypoechoic region of an ultrasound image.
Figure 4B:
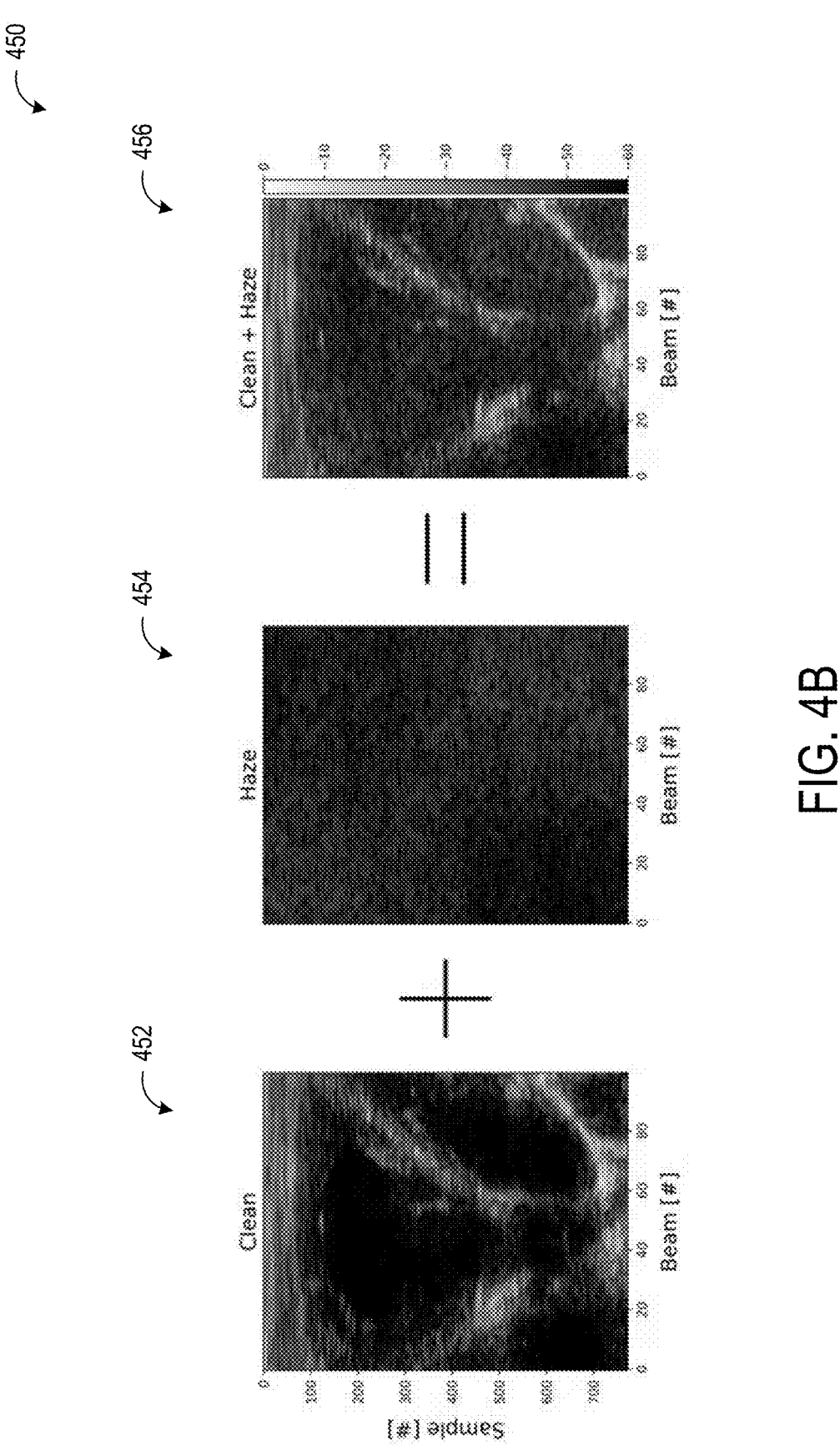
FIG. 4B shows an ultrasound image generated by superimposing a stacked, extracted haze patch on a haze-free image.

Referring to FIG. 3A, an example of an artifact reduction network training system 300 is shown. Artifact reduction network training system 300 may be implemented by one or more of an image processing system, such as image processing system 202 of FIG. 2, to train a data-driven model to reduce an amount of clutter artifacts (e.g., haze) in one or more ultrasound images. In an embodiment, artifact reduction network training system 300 includes an artifact reduction network 302, to be trained, which may be part of a model module 392 of the image processing system (e.g., model module 208 of FIG. 2).

The artifact reduction network may be trained on a training dataset, which may be stored in a training module 394 (e.g., training module 210 of FIG. 2). The training dataset may comprise a plurality of training pairs 306. Each training pair 306 may comprise an input image sequence 372 and a target (e.g., ground truth) image sequence 374, which may be generated from ultrasound image sequences acquired via an imaging device 308. As described above, in some embodiments, input image sequence 372 and target image sequence 374 may comprise raw image data from a stage of an acquisition chain of the ultrasound images prior to image reconstruction.

In one example, the ultrasound image sequences may be acquired via an ultrasound probe (e.g., ultrasound probe 236 of FIG. 2) of an ultrasound imaging system (e.g., ultrasound imaging system 100 of FIG. 1) during an examination of one or more anatomical structures of a patient. The ultrasound image sequences may also be obtained from an image dataset 310, which may be generated from various examinations performed on subjects (e.g., by imaging device 308). Alternatively, in some embodiments, image dataset 310 may be an external image dataset, such as a public dataset of ultrasound image sequences.

Training module 394 may include a dataset generator 312, where input image sequence 372 and target image sequence 374 may be selected and/or generated from the ultrasound images and paired by dataset generator 312. In various embodiments, training module 394 may include a classifier 314, which may classify the sequences of the ultrasound images in image dataset 310 based on amount of clutter artifacts included in the sequences of images. Specifically, classifier 314 may classify the image sequences in image dataset 310 into a first set of lower-clutter sequences 316, or a second set of higher-clutter sequences 318, or a third set of moderate-clutter sequences. Lower-clutter image sequences 316 may include images with a level of clutter deemed to be insignificant (e.g., below a first threshold amount of clutter), while higher-clutter image sequences 318 may include images with a level of clutter deemed to be excessive (e.g., greater than a second, higher threshold amount of clutter). The threshold may be chosen at a level where clutter is not visible inside hypoechoic regions of the image when the image has subsequently undergone standard pre- and post-compression mapping amplitudes to display gray values.

If the amount of clutter artifacts in an ultrasound image is less than the first, lower threshold, the ultrasound image may be assigned to the lower-clutter image sequences 316. If the amount of clutter artifacts in the ultrasound image is greater than the second, higher threshold, the ultrasound image may be assigned to the higher-clutter image sequences 318. The moderate-clutter sequences may include images with levels of clutter not deemed to be either insignificant or excessive, and may be discarded. The lower-clutter image sequences 316 and the higher-clutter image sequences 318 may be used by dataset generator 312 in the generation of training pairs 306.

In some embodiments classifier 314 may classify the images based on an output of a machine learning (ML) model trained to quantify an amount of clutter artifacts present in an ultrasound image, or a rules-based system. In other embodiments, the ultrasound images may be classified into the lower-clutter image sequences 316 and the higher-clutter image sequences 318 manually, by human experts.

During generation of the training pairs 306, clutter artifacts present in higher-clutter images of the higher-clutter image sequences 318 may be extracted and used to generate artifact overlays that may be applied to corresponding lower-clutter images of the lower-clutter image sequences 316. In other words, input/target pairs of image sequence may be generated, where each pair includes a target image sequence 374 drawn from the lower-clutter image sequences 316, and a corresponding input image sequence 372 created by superimposing on target image sequence 374 an artifact overlay generated from a higher-clutter image drawn from higher-clutter image sequences 318. Generation of training pairs 306 by dataset generator 312 is described in greater detail below in reference to FIG. 3B.

Once the training pairs 306 have been generated, the training pairs 306 may be assigned to either a training dataset, validation dataset, or a test dataset. The training dataset may be used for the optimization of a data driven model. The validation dataset may be used for model selection to prevent overfitting, whereby artifact reduction network 302 learns to map features specific to samples of the training set that are not present in the validation set. The test dataset may be used to estimate the model's performance in deployment. The number of training pairs 306 in the test and validation datasets may be less than the number of training pairs 306 in the training dataset.

In some embodiments, the training pairs 306 may be randomly assigned to either the training dataset, the validation dataset, or the test dataset in a pre-established proportion. For example, 80% of the training pairs 306 generated may be assigned to the training dataset, and 10% of the training pairs 306 generated may be assigned to the validation and test dataset each. In other embodiments, different proportions of training pairs 306 may be assigned to the training dataset, validation dataset, and the test dataset. It should be appreciated that the examples provided herein are for illustrative purposes, and the training pairs 306 may be assigned to the training dataset, validation dataset, or the test dataset via a different procedure and/or in a different proportion without departing from the scope of this disclosure.

Artifact reduction network training system 300 may be implemented to train artifact reduction network 302 to learn to reduce an amount of clutter artifacts from ultrasound images. Artifact reduction network 302 may be configured to receive the training pairs 306 from the training module 304, where the input image sequence 372 and the corresponding target image sequence 374 are inputted into artifact reduction network 302. Target image sequence 374 may be a lower-clutter image sequence, and input image sequence 372 may be a higher-clutter image sequence generated from target image sequence 374 by dataset generator 312. In other words, input image sequence 372 may be target image sequence 374 with a superimposed artifact overlay.

Artifact reduction network 302 may output an ultrasound image sequence with a lower amount of clutter artifacts than input image sequence 372. Artifact reduction network 302 may then iteratively adjust one or more parameters of artifact reduction network 302 in order to minimize a loss function based on a difference between the outputted ultrasound image sequence and target image sequence 374, until an error rate decreases below a first threshold error rate. Training of artifact reduction network 302 is described in greater detail below, in reference to FIG. 5.

In various embodiments, input image sequence 372 and target image sequence 374 may comprise a plurality of consecutive frames of two dimensional (2D) images, where a first number of frames included in input image sequence 372 may be equal to a second number of frames included in target image sequence 374. Thus, input image sequence 372 and target image sequence 374 may be inputted into artifact reduction network 302 as spatio-temporal three dimensional (3D) data objects including two dimensions of image values (e.g., pixels with an x position and a y position) and time as the third dimension, represented by the consecutive frames. In other words, each data value of each pixel of each frame of each image sequence may be inputted into an input node of artifact reduction network 302.

Artifact reduction network training system 300 may include a validator 320 that validates a performance of artifact reduction network 302. Validator 320 may take as input a trained or partially trained artifact reduction network 302 and a validation dataset of training pairs 306. If the error rate of the trained or partially trained artifact reduction network 302 on the validation dataset of training pairs 306 decreases below a second threshold error rate, the performance of the trained or partially trained artifact reduction network 302 may be validated, whereby a training stage of the trained or partially trained artifact reduction network 302 may end.

Artifact reduction network training system 300 may include an inference module 396, which comprises a validated artifact reduction network 322 that has been validated by validator 320 as described above. Inference module 396 may also include instructions for deploying validated artifact reduction network 322 to reduce an amount of clutter artifacts in one or more new input image sequences (e.g., generated by imaging device 308, or stored in a second image dataset). Specifically, validated artifact reduction network 322 may receive new input image sequences as input, and may output a set of reduced-clutter image sequences 326, where reduced-clutter images 326 are versions of the new input images with a reduced amount of clutter. For example, the reduce-clutter image sequences 326 may have an amount of clutter that is similar to images of the lower-clutter image sequences 316.

Referring to FIG. 3B, a block diagram 350 shows an example of how training pairs 306 of FIG. 3A are generated from a first set of lower-clutter image sequences 316 and a second set of higher-clutter image sequences 318. As described above, training pairs 306 may be generated to train an artifact reduction network, such as artifact reduction network 302 of FIG. 3A, to reduce an amount of clutter artifacts in ultrasound image sequences. The processes depicted in FIG. 3B may be performed within a training module of an image processing system, such as training module 394 of image processing system 202 of FIG. 2. Additionally, some portions of the processes depicted in FIG. 3B may be performed by human experts in one or more manual steps, as indicated below.

During a haze extraction process 352, a plurality of haze patches 354 may be extracted from hypoechoic regions of the higher-clutter image sequences 318. In various embodiments, haze extraction process 352 may be a manual process performed by the human experts. Extraction of the haze patches is described in greater detail below, in reference to FIG. 6.

During an artifact overlay generation process 356, the plurality of haze patches 354 may be processed to generate a plurality of artifact overlays 358. Each artifact overlay 358 may include an amount of clutter data, which may be added to raw image data of a lower-clutter target image sequence to generate a higher-clutter version of the target image sequence. The generated higher-clutter image sequence and the lower-clutter target image sequence may then constitute an image pair for training the artifact reduction network. The artifact overlay generation process 356 is described in greater detail below, in reference to FIG. 6.

Once the artifact overlays 358 have been generated, a higher-clutter image sequence generator 360 may apply the artifact overlays 358 to images of lower-clutter image sequences 316 (e.g., resulting from the initial classification of the images and image dataset 310) to create a set of generated higher-clutter image sequences 362. Since higher-clutter image sequences 362 are constructed from lower-clutter image sequences 316 with a superimposed clutter overlay, a frame-to-frame temporal consistency between structural information in the lower-clutter and higher-clutter image sequences of a training pair 306 may be guaranteed. Additionally, the temporal consistency between an artifact overlay (containing clutter) and an underlying lower-clutter image may be maintained by using an ECG signal to coordinate use of clutter images from a same phase of a heart cycle of a subject as the lower-clutter image it is superimposed over. Time interpolation may be also be used to improve the temporal consistency. Thus, a training pair 306 may include a lower-clutter image sequence 316 as a target image sequence 374, and a generated higher-clutter sequence 362 as an input image sequence 372, where the generated higher-clutter image sequence 362 is the lower-clutter image sequence 316 with one or more artifact overlays 358 superimposed on it. The lower-clutter image sequence may include unaltered raw image data. The lower-clutter image sequence may not include artificial or synthetic image data or image data that is processed, adjusted, enhanced, reduced or transformed from raw image data acquired from a subject via an imaging device. In this way, a set of training pairs 306 may be generated based on real (e.g., not synthetically generated) ultrasound images with varying amounts of added realistic clutter artifacts.

Figure 5:
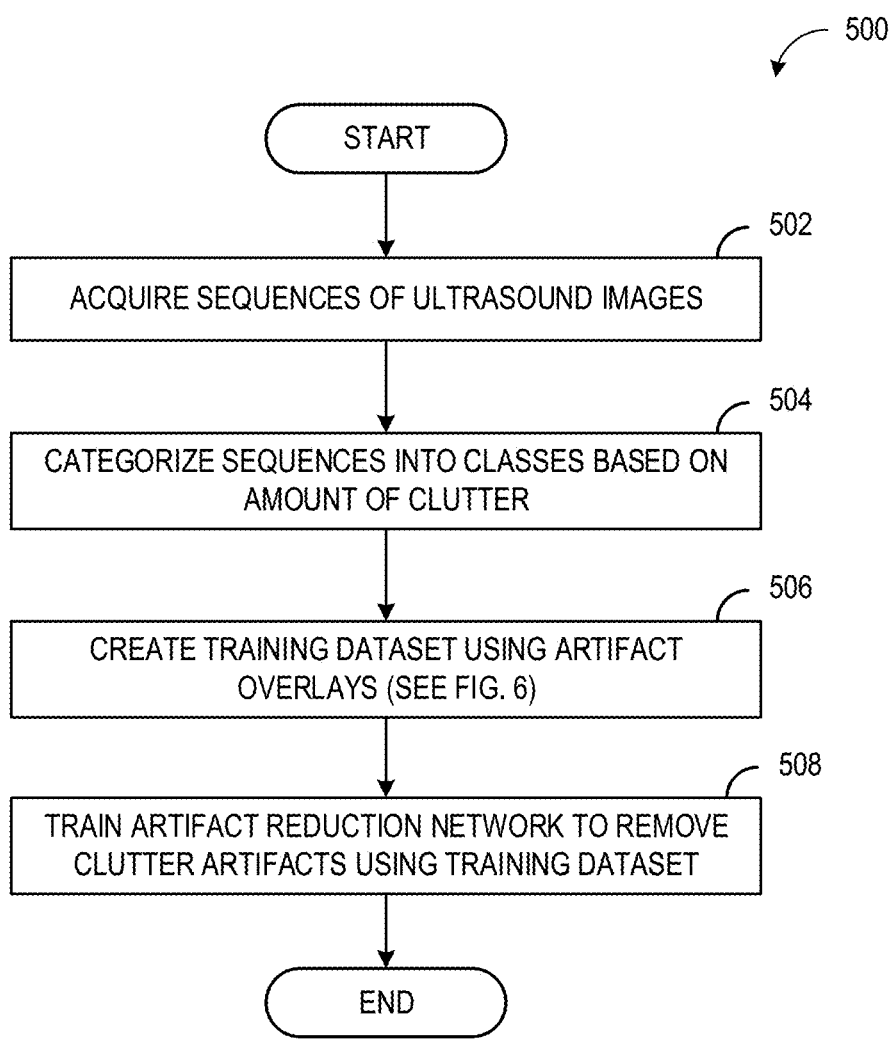
FIG. 5 is a flowchart illustrating an exemplary procedure for training the artifact reduction network.

Referring now to FIG. 5, an exemplary method 500 is shown for training an artifact reduction network (e.g., artifact reduction network 302 of FIG. 3A) to reduce an amount of clutter in sequences of ultrasound images. Method 500 may be carried out by a training module and/or a model module of an artifact reduction network training system, such as training module 394 and model module 392 of artifact reduction network training system 300. The artifact reduction network training system may be included in an image processing system, such as image processing system 202, and one or more instructions of method 500 may be executed by a processor of the image processing system (e.g., processor 204).

Method 500 begins at 502, where method 500 includes acquiring sequences of ultrasound images. The sequences of images may be acquired via an imaging device, such as imaging device 308, from an image dataset (e.g., image dataset 310) generated by the imaging device, or via a different source.

At 504, method 500 includes categorizing the sequences of ultrasound images into classes based on an amount of clutter included in the images of the sequences. In various embodiments, the categorization may be performed by human experts, based on predetermined clutter thresholds. For example, a first image reviewed by a human expert may include a first amount of clutter that is less than a first clutter threshold defining an insignificant amount of clutter. A second image reviewed by the human expert may include a second amount of clutter that is greater than the first clutter threshold, but less than a second clutter threshold defining an excessive amount of clutter. A third image reviewed by the human expert may include a third amount of clutter that is greater than the second clutter threshold. The first image may be categorized as having an insignificant amount of clutter; the third image may be categorized as having an excessive amount of clutter; and the second image may be categorized as having an amount of clutter that is either insignificant or excessive, whereby the second image may be discarded. In some embodiments, a training module of the neural network training system may include a classifier that may automatically classify the sequences of ultrasound images into the classes.

At 506, method 500 includes creating a training dataset using artifact overlays. Creating the training set using artifact overlays is described in greater detail below, in reference to FIG. 6.

Figure 6:
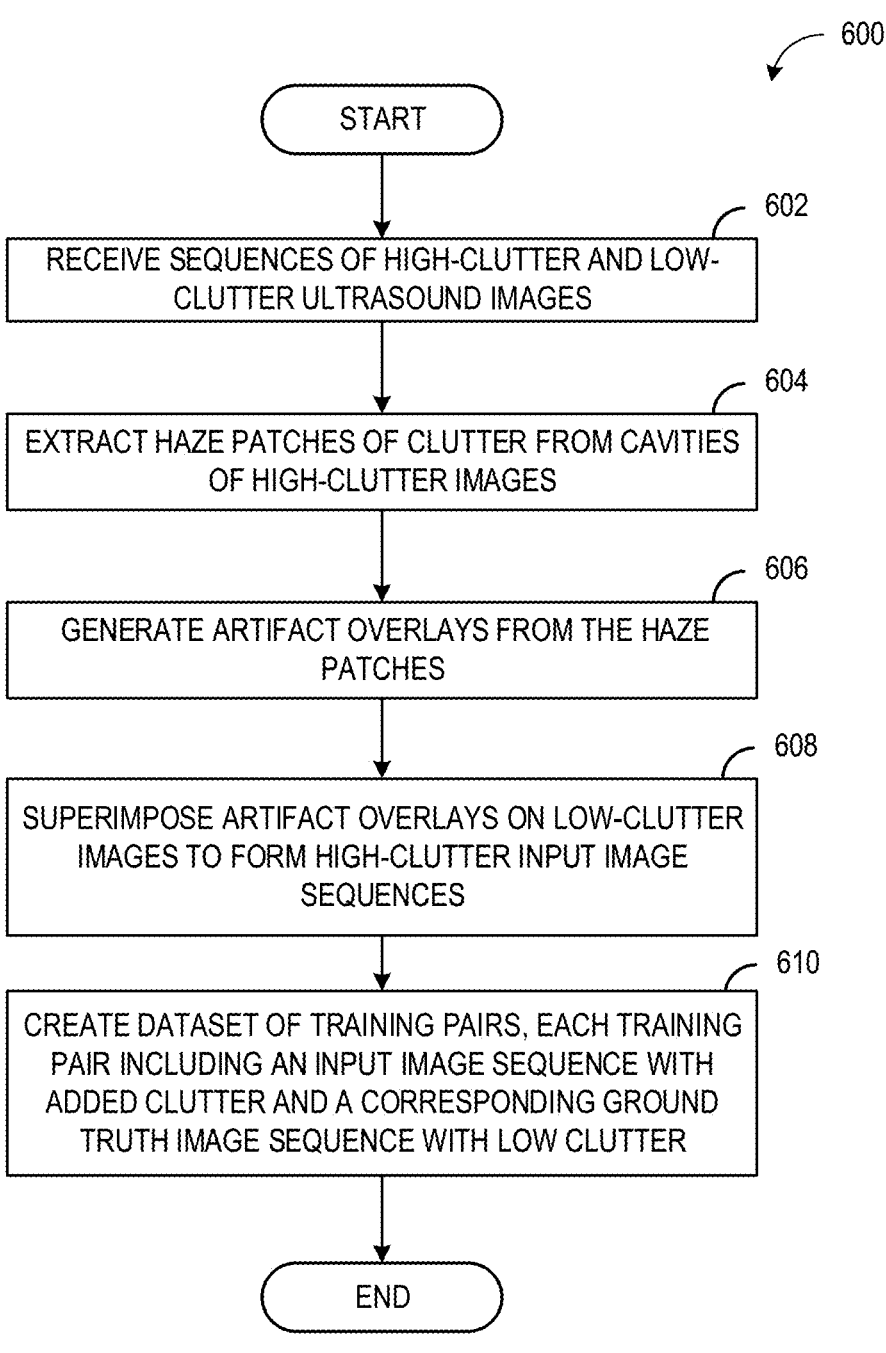
FIG. 6 is a flowchart illustrating an exemplary procedure for generating a training dataset for training the artifact reduction network.

Referring now to FIG. 6, an exemplary method 600 is shown for generating a training dataset for training an artifact reduction network (e.g., artifact reduction network 302 of FIG. 3A) to reduce an amount of clutter from ultrasound image sequences. The training dataset may comprise a plurality of training pairs, such as the training pairs 306 described above in reference to the artifact reduction network training system 300. Method 600 may be carried out by a training module of an artifact reduction network training system, such as training module 394 of the artifact reduction network training system 300. The artifact reduction network training system may be included in an image processing system, such as image processing system 202, and one or more instructions of method 500 may be executed by a processor of the image processing system (e.g., processor 204).

Method 600 begins at 602, where method 600 includes receiving sequences of higher-clutter ultrasound images and lower-clutter ultrasound images. As described above, the higher and lower-clutter image sequences may be extracted from an ultrasound image dataset (e.g., image dataset 310 of FIG. 3A) by one or more human experts, or by a classifier component of the training module.

At 604, method 600 includes extracting patches of clutter from cavities of images included in the higher-clutter image sequences. Each image of the higher-clutter image sequences may include portions showing anatomical structures of a scanned subject, and portions with no anatomical structures. For example, an image of a heart of the scanned subject may include structural features of the heart, and various cavities of the heart where no structural data is included. In the cavities and/or other areas where no structural data is included, a haze (e.g., an amount of noise) may be visible, where the haze may include clutter artifacts. An amount of the clutter artifacts may be high, or the amount may be low. If the amount of clutter artifacts is high, an examiner may find it difficult to view the structural features relevant to a diagnosis or purpose of a relevant ultrasound exam. Therefore, partially or totally removing the clutter artifacts may make it easier for the examiner to view the structural features.

In the areas of an image where no structural data is included, an area referred to herein as a haze patch may be defined by a bounding box or polygon. While raw image data outside of the patch may include structural features of interest, the raw image data included within the patch may be assumed to be artifacts (e.g., clutter) and not structural features. However, a placement of the bounding box or polygon may be maintained across a plurality of images included in a sequence, wherein each image of the sequence, the bounding box or polygon is positioned at a same location. During the sequence, the structural features may move. For example, during a heart cycle, at some point in time the heart may be contracting, while at other points in time the heart may be expanding. As the structural features move, elements of the structural features may enter the bounding box in one or more images of the sequence.

To ensure that the haze patches including the clutter do not include the structural features, the images included in the sequence may be individually reviewed by human experts, and a polygon binary weighting scheme may be used to segment areas within each patch verified as not including the structural features. A weighting mask may be generated for a patch, where data obscured by portions of the mask may not be included in the patch, and data not obscured by portions of the mask may be included in the patch. The mask can also be used to guide the loss function during training of the artifact reduction network, where the mask is applied to both an artifact-reduced image and the target image prior to a calculation of the loss function during training of the data driven model. For example, the mask may be included as a component of the loss function, where the mask may be multiplied by image sequence data outputted by the artifact reduction network and the target image sequence data prior to calculating a difference between the image sequence data and target image sequence data. The mask may comprise a three dimensional array of zeros and ones, such that when the mask is multiplied by the 3D image sequence (e.g., a plurality of frames of 2D images), data values of the 3D output image sequence corresponding to the structural features are suppressed (e.g., multiplied by zeros of the mask), and data values of the 3D output image sequence not corresponding to the structural features are not suppressed (e.g., multiplied by ones of the mask). In other words, the mask is intended to have the effect of not including pixels corresponding to structural elements (coming from the haze patches) in the loss function. The mask is used to set a difference between a filtered output and a reference for the pixels to zero. This can be achieved by setting the pixel values to zero in the filtered image and the reference (using the mask) prior to calculating the loss. These pixels will then have no contribution, as $0-0=0$. In this way, structural elements included in the artifact overlays may not affect training of the artifact reduction network.

FIG. 4A shows an example haze patch extraction diagram 400, where a haze patch 406 is extracted from a hypoechoic region of an ultrasound image, such as a heart. Haze patch extraction diagram 400 includes an ultrasound image 401, which may be included in a sequence of ultrasound images including a high amount of haze (e.g., noise artifacts), such as a higher-clutter sequence 318 of FIG. 3A. Ultrasound image 401 includes structural elements of the heart, which appear as lighter sections of ultrasound image 401. For example, a wall 407 of the heart may be seen in ultrasound image 401. A cavity 403 of the heart is also shown, which appears as a darker section. A bounding box 404 is drawn at a location within cavity 403 where few or no structural elements are found. In other words, an area 405 within bounding box 404 may include clutter artifacts, and may not include the structural elements, or may include structural elements of a small size. Bounding box 404 may have a width 430 and a height 432. In other embodiments, bounding box 404 may not be rectangular (e.g., a polygon).

Haze patch 406 is extracted from ultrasound image 401 at the location of bounding box 404, as indicated. Because haze patch 406 does not include the structural elements, haze patch 406 may show a general level of clutter or haze that is distributed across ultrasound image 401. The haze may be equally distributed across ultrasound image 401, or the haze may be greater or lesser in different portions of ultrasound image 401. Further, an amount of the haze may vary over time.

Bounding box 404 may be maintained at the same location over a plurality of images (e.g., frames) of the sequence from which ultrasound image 401 was drawn, such that a haze patch (e.g., haze patch 406) may be extracted from each frame of the sequence at the same location. Over the course of the sequence, the heart may be beating. As the heart is beating, the structural elements of the heart including wall 407 may move, such that a position of the structural elements within ultrasound image 401 may shift between the frames of the sequence. As a result, portions of the structural elements may be present or absent in a given ultrasound image. For example, in a first frame of the sequence, no structural elements may be present in bounding box 404; in a second frame of the sequence, a portion of the structural elements may be present in bounding box 404; in a third frame of the sequence, no structural elements may be present in bounding box 404; and so on. Therefore, each frame of the sequence may be reviewed by human experts to determine whether structural elements are present in bounding box 404.

Haze patch extraction diagram 400 includes an ultrasound image 402, where image 402 is a duplicate of ultrasound image 401. In ultrasound image 402, a first anatomical structure 412 and a second anatomical structure 414 are included in bounding box 404. Additionally, the human experts may not be certain whether structural elements are found in a first portion 413 of ultrasound image 402 within bounding box 404, or in a second portion 415 of ultrasound image 402 within bounding box 404. To ensure that haze patch 406 includes haze and not structural elements, the human experts may define an area within bounding box 404 with a high probability of not including the structural elements via a polygon 410.

A mask 425 may then be created based on polygon 410, which applies a polygon weighting scheme to distinguish non-structural haze data from data possibly including the structural elements. Mask 425 may be a matrix of values corresponding to pixels of area 405 within bounding box 404. For example, mask 425 may include values of zero or one, where dark portions of mask 425 are assigned zeros, and light portions of mask 425 are assigned ones. Thus, mask 425 includes a first area 420 corresponding to polygon 410 including the non-structural haze data where ones have been assigned; a second area 416 corresponding to first anatomical structure 412, where zeros have been assigned; a third area 418 corresponding to second anatomical structure 414, where zeros have been assigned; a third area 422 corresponding to first portion 413, where zeros have been assigned; and a fourth area 424 corresponding to second portion 415, where zeros have been assigned.

Mask 425 may then be used to guide the optimization of the model, or multiplied by pixel values of raw image data of haze patch 406. Where a pixel of mask 425 includes a zero, the pixel may not be included in the objective function as the pixel may be part of an anatomical structure, or the raw image data of haze patch 406 may be suppressed. Where a pixel of mask 425 includes a one, the raw image data of haze patch 406 may include haze and be used to guide the optimization of the model. In this way, mask 425 may be used to remove (e.g., hide) any structural elements detected in an ultrasound image within bounding box 404.

For the extraction of haze patch 406 and a generation of mask 425, as also regards lower-clutter underlay data, the raw image data format of ultrasound images 401 and 402 may be linear domain amplitude beamformed IQ (complex) data in beamspace, where raw data acquired via an ultrasound probe in a scan is arranged in a rectangular shape where beam data is represented vertically and the horizontal axis is scan angle or beam index.

Since the raw data resides as beam space data, a rectangular bounding box 404 may be used for extracting haze patch 406. Additionally, as a result of the rectangular shape of haze patch 406, haze patch 46 may be stacked to efficiently cover a lower-clutter ultrasound image, as described in greater detail below. However, in some embodiments, the input and target images included in training pairs of the artifact reduction network may be scan-converted prior to a training stage. An advantage of scan conversion is that the training pair image sequences (and subsequently the input image sequence) exhibit geometries that match an actual physical object without distortion. A disadvantage of scan conversion may be that a point spread function of an imaging apparatus may be less uniform across an image, leading to lower resolution in the far field than in the near field. In other embodiments, scan converted data, log compressed data, envelope data, or channel data may be used.

Returning to method 600, at 606, method 600 includes generating a plurality of artifact overlays from the haze patches. Each artifact overlay of the plurality of artifact overlays may be an image of a same size as a lower-clutter ultrasound image (e.g., an image of lower-clutter sequences 316 of FIG. 3B) to be used in a sequence for a training pair for training the artifact reduction network, where the ultrasound image is composed entirely of clutter artifacts (e.g., haze) and includes no structural elements. Thus, generating the artifact overlays may include positioning a plurality of haze patches to cover the lower-clutter ultrasound image (e.g., an image of lower-clutter sequences 316 of FIG. 3B). The plurality of haze patches may be positioned to minimize a space between each haze patch. In examples where a rectangular bounding box is used, the artifact overlay may be a collection of copies of a haze patch or haze patches taken from different higher-cluttered image sequences, where each haze patch is positioned such that each edge of the haze patch is aligned with either an edge of the artifact overlay or an edge of an adjacent haze patch, with no space in between (e.g., in a tiled arrangement). Haze patches from the same higher-cluttered image sequence may also be stacked along the time (frame) dimension in order to capture changes over time of the cluttered artifacts. In order to increase the divergency of the generated artifact overlays, it is also possible to have two or more haze patches spatially overlapping.

For example, a haze patch may have a height (e.g., height 432 of FIG. 4A) and a width (e.g., width 430 of FIG. 4A).

If the height of the lower-clutter ultrasound image is four times the height of the haze patch, then four haze patches may be stacked vertically to form a column that extends over the full height of the lower-clutter ultrasound image. Similarly, if the width of the lower-clutter ultrasound image is four times the width of the haze patch, then four haze patches may be stacked horizontally to form a row that extends over the full width of the lower-clutter ultrasound image. In this way, a plurality of haze patches may be combined and positioned to cover the lower-clutter ultrasound image with haze. For each haze patch, a corresponding mask may be included (e.g., mask 425), to ensure that structural elements of the higher-clutter ultrasound images from which the haze patches were extracted can be tracked and utilized during the model optimization.

Generating the artifact overlays may also include augmenting or adjusting the haze patches. For example, prior to stacking a haze patch, a size of the haze patch may be increased or decreased such that the haze patch may be expanded (e.g. stretched) or contracted (e.g., compressed) in either or both of a horizontal or vertical dimension. For example, the width or the height of the lower-clutter ultrasound image may not be divisible by the width or the height of the haze patch, and the width and/or the height of the haze patch may be increased or decreased to facilitate efficient stacking of the haze patch to cover the lower-clutter ultrasound image. Other augmentations include general morphing and assigning different strength to the overlay (e.g., gain adjusting) and translating the patches horizontally or vertically. Augmentations may also be applied along the time (frame) dimension of the image sequences. The advantage of augmenting the data is to increase a diversity of haze data of the haze patches (e.g., the number of diverse overlays from the amount of patch data that exists), thus allowing the network to generalize more effectively.

At 608, method 600 includes superimposing the artifact overlays on images of the lower-clutter image sequences to form ultrasound images with a high degree of clutter. An artifact overlay created for a first image of a lower-clutter image sequence may be used on other images of the low clutter image sequence. The artifact overlays may be superimposed on lower-clutter ultrasound image sequences to generate a corresponding set of higher-clutter ultrasound image sequences (e.g., generated higher-clutter sequences 362) with varying amounts of clutter artifacts, depending on an amount of haze included in each artifact overlay used to generate each higher-clutter ultrasound image of the set of higher-clutter ultrasound image sequences.

Turning to FIG. 4B, an exemplary artifact overlay superimposition 450 is shown. Exemplary artifact overlay superposition 450 includes a lower-clutter ultrasound image 452, such as an image included in lower-clutter sequences 316 of FIG. 3A, and an artifact overlay 454 generated by stacking a plurality of augmented copies of one or more haze patches including an amount of clutter artifacts. The haze patches may be extracted from one or more higher-clutter ultrasound images, such as higher-clutter ultrasound image 401 of FIG. 4A, which may be included in higher-clutter sequences 318). As depicted in FIG. 4B, artifact overlay 454 may be superimposed upon lower-clutter ultrasound image 452 to generate a higher-clutter ultrasound image 456 that includes both the structural elements seen in image 452 and the haze of artifact overlay 454. Lower-clutter ultrasound image 452 and higher-clutter ultrasound image 456 may be a first set of paired images of a training pair for training an artifact reduction network, such as a training pair 306 of artifact reduction network training system 300. Specifically, higher-clutter ultrasound image 456 may be a frame within an image sequence used by the artifact reduction network (e.g., input image sequence 372), and lower-clutter ultrasound image 452 may be a target frame (e.g., of target image sequence 374) in the ground truth image sequence target image sequence 374.

Returning to method 600, when the artifact overlays are superimposed on the lower-clutter images, raw image data of the artifact overlays may be added or combined with raw image data of the lower-clutter images. As a result of adding the raw image data of an artifact overlay to the raw image data of a lower-clutter image, a higher-clutter ultrasound image may be generated that may be very similar to an ultrasound image naturally including a high amount of clutter (e.g., such as an image included in a higher-clutter sequence 318 of FIG. 3B).

At 610, method 600 includes creating a dataset of training pairs, where each training pair includes one input image sequence with clutter added via the artifact overlay, and a corresponding ground truth image sequence with low clutter. The training pairs may include input image sequences with varying amounts of added haze. The training pairs may be organized in sequences with an order that corresponds to an order of the lower-clutter image sequences and/or an order of the higher-clutter image sequences acquired during generation of the ultrasound image dataset used to generate the training pairs (e.g., image dataset 310 of FIG. 3A).

It should be appreciated that in addition to generating training data in the manner described above, other types of training data may be combined to increase a diversity of the artifact data. For example, in some embodiments, the training data generated as described above may be combined with training data created by an acoustic wave simulation, or training data generated in a different manner.

Returning to FIG. 5, at 508, method 500 includes training the artifact reduction network to remove clutter artifacts from ultrasound images, using the training dataset generated at 506 and described in reference to method 600. In various embodiments, the artifact reduction network may be a deep learning (DL) neural network. In one embodiment, the artifact reduction network is a spatio-temporal 3D deep CNN, where 3D refers to a sequence of 2D images with time being a third dimension. During an ultrasound examination, a location of target structures of a region of interest (ROI) within the 2D ultrasound images may shift, due to beating of a subject's heart, movement of the subject's lungs while breathing, etc. However, clutter artifacts present in the ultrasound images may not move, or may move in a different manner and/or direction. Because a temporal evolution of the 2D ultrasound images over time may aid the CNN in distinguishing the clutter artifacts from the target structures, the temporal evolution is captured by the CNN to remove or reduce an amount of haze from 2D ultrasound images. In other words, the CNN may be trained to perform a signal separation of time sequences of ultrasound 2D data including haze.

The CNN can be trained to perform this video separation based on a specific number N of input frames in sequence. In one embodiment, the CNN is trained to use a number of frames prior to the desired artifact reduced output frame for each consecutive output frame. This embodiment may be preferred for not causing a lag in time between the acquisition and the displayed output image. In another embodiment, the CNN may use a number of frames prior to and a number of frames after the desired reduced artifact output frame, for each consecutive output frame. This embodiment will give a small lag between the time of acquisition and the displayed image, but may be preferred, for example, if the artifact reduction network yields an improved performance. In any case, the system may continuously accumulate in a running buffer the latest N frames relied on by the CNN to infer the latest artifact reduced output frame in a sequence.

The CNN may include one or more convolutional layers, which in turn comprise one or more convolutional filters. The convolutional filters may comprise a plurality of weights, wherein the values of the weights are learned during a training procedure. The convolutional filters may correspond to one or more visual features/patterns, thereby enabling the artifact reduction network to identify and extract features from the images.

Training the artifact reduction network may include iteratively inputting image sequences of corresponding training image pairs (e.g., an input image sequence 372 of a training pair 306) into an input layer of the artifact reduction network. The artifact reduction network maps an input image sequence to an output image sequence by propagating the input image sequence from the input layer, through one or more hidden layers, until reaching an output layer of the artifact reduction network. In some embodiments, the output of the artifact reduction network comprises a 3D matrix of values, wherein each value corresponds to a distinct intensity of a pixel of the output images at a point in time, and wherein the distinct intensity of each pixel of the output images generates a reconstruction of the input images where an amount of haze in one or more regions of the output images are lower than an amount of haze in the one or more regions of the input images.

As mentioned above, the sample data format may be different in different embodiments. What hitherto has been called an image in the example figures has been displayed as a real valued log compressed set of data points. This has been done for illustrational purposes, as this format resembles a final output to a display device. However, in a preferred embodiment, the image data format seen by the training network, both for the lower-clutter image sequences and the higher-clutter overlays, is complex in-phase/quadrature (IQ) data without log compression or envelope detection. This may be considered preferable, since in this representation, the reverberation artifacts that are desired to be removed may be linearly additive, and because a precision in localization and movement of image constituents may be more accurate before envelope detection. However, in other embodiments, real-valued envelope data may be employed. In yet other embodiments, log compressed amplitudes may be used in the training and later inference. Moreover, an alternative embodiment could use channel data containing acquired data for each transducer element for a plurality of transmit events in the scan. The extraction of clutter signals would then be a more elaborate process, entailing comparing which channel data components contribute to what parts of the beamformed image. In yet other embodiments, the input image data may be RF data. As has been mentioned above, beamformed IQ data may be scan-converted prior to being inputted into the artifact reduction network.

The artifact reduction network may be configured to iteratively adjust one or more of the plurality of weights of the artifact reduction network in order to minimize a loss function, based on an assessment of differences between the input image sequence and the target image sequence (e.g., target image sequence 374) comprised by each image sequence pair of the training image pairs. In one embodiment, the loss function is a Mean Absolute Error (MAE) loss function, where differences between the input image sequence and the target image sequence are compared on a pixel-by-pixel basis and summed. In another embodiment, a different loss function may be used, such as a Structural Similarity Index (SSIM), an adversarial loss, or different type of loss function. Various loss functions can also be combined together to form the training objective. It should be appreciated that the examples provided herein are for illustrative purposes, and other types of loss functions may be used without departing from the scope of this disclosure.

The weights and biases of the artifact reduction network may be adjusted based on a difference between the output image sequence and the target (e.g., ground truth) image sequence of the relevant training pair. The difference (or loss), as determined by the loss function, may be back-propagated through the artifact reduction network to update the weights (and biases) of the hidden (convolutional) layers. In some embodiments, back propagation of the loss may occur according to a gradient descent algorithm, wherein a gradient of the loss function (a first derivative, or approximation of the first derivative) is determined for each weight and bias of the deep neural network. Each weight (and bias) of the artifact reduction network is then updated by adding the negative of the product of the gradient determined (or approximated) for the weight (or bias) with a predetermined step size. Updating of the weights and biases may be repeated until the weights and biases of the artifact reduction network converge, or the rate of change of the weights and/or biases of the deep neural network for each iteration of weight adjustment are under a threshold. It should also be noted that back-propagation is used as an example, and that other optimization schemes are valid for fitting the artifact reduction network's parameters.

In order to avoid overfitting, training of the artifact reduction network may be periodically interrupted to validate a performance of the artifact reduction network on the validation image pairs, as described above in reference to FIG. 3A. Training of the artifact reduction network may end when a performance of the artifact reduction network on the validation image sequence pairs converges (e.g., when an error rate on the validation set converges on or to within a threshold of a minimum value). In this way, the artifact reduction network may be trained to reconstruct an input image sequence during an inference stage, where the reconstructed image sequence includes less haze than the input image.

After the artifact reduction network has been trained and validated, the trained artifact reduction network may be stored in a memory of the image processing system for use in ultrasound examinations during a subsequent inference stage. For example, the trained artifact reduction network may be stored in an inference module of the image processing system (e.g., inference module 212).

Figure 7:
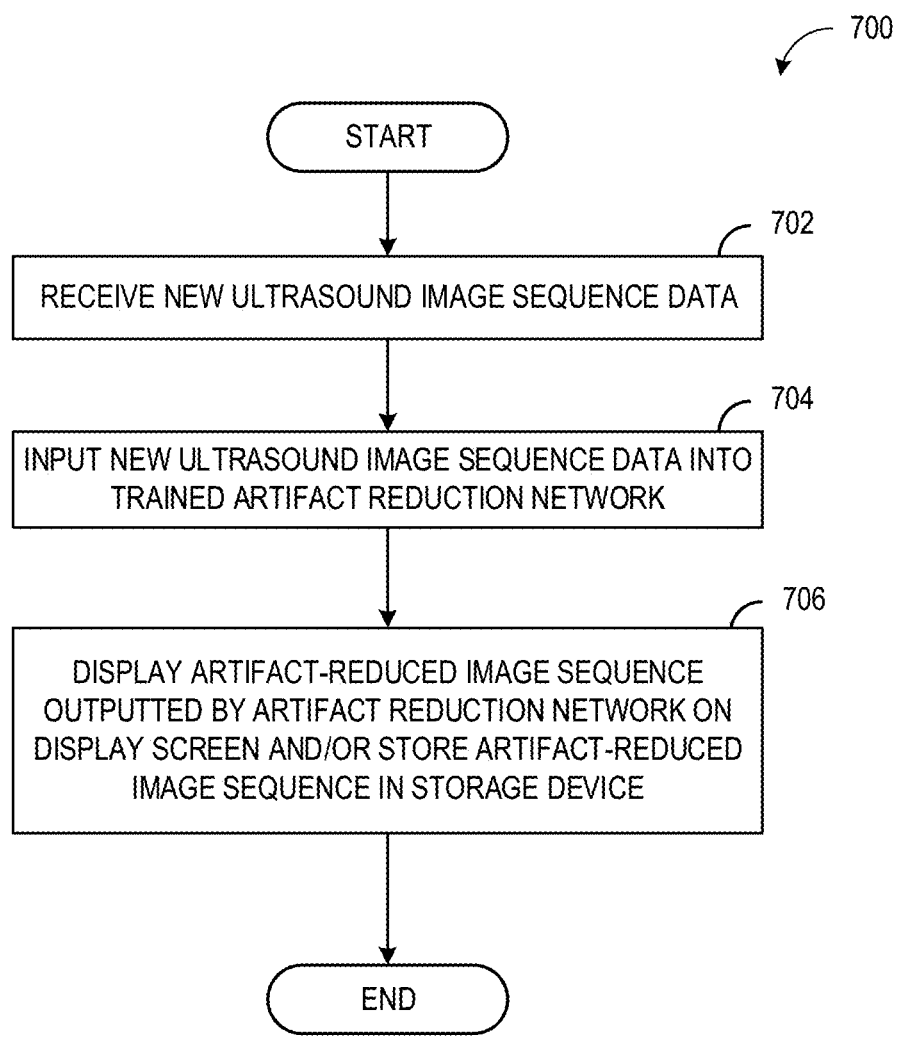
FIG. 7 is a flowchart illustrating an exemplary procedure for using the artifact reduction network to remove artifacts from one or more ultrasound images using a trained artifact reduction network.
Figure 8:
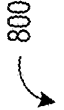
FIG. 8 shows an example lower-clutter ultrasound image where artifacts have been removed from a cluttered ultrasound image.
Figure 8:
Figure 8:
Figure 8:
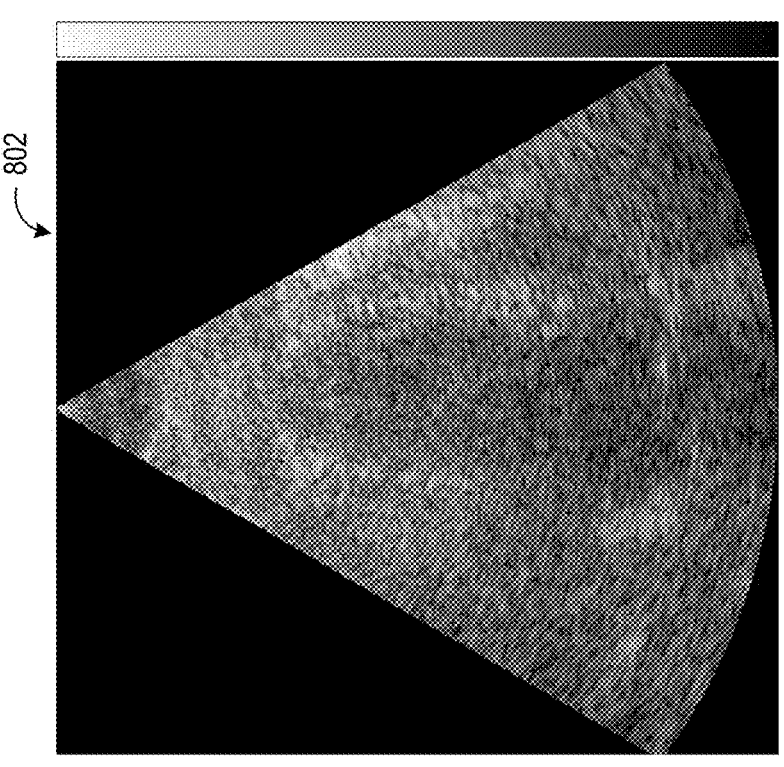

Referring now to FIG. 7, an exemplary method 700 is shown for generating artifact-reduced images using a trained artifact reduction network, such as the artifact reduction network described above in reference to FIG. 6 (e.g., artifact reduction network 302 of FIG. 3A). Method 700 may be performed within an inference module of an image processing system, such as inference module 212 of image processing system 202 of FIG. 2 and/or inference module 396 of FIG. 3A.

Method 700 begins at 702, or method 700 includes receiving new ultrasound image sequence data. The new ultrasound image sequence data may be generated by an imaging device (e.g., imaging device 308 of FIG. 3A), or the new ultrasound image sequence data may be stored in a memory of the image processing system (e.g., image database 214).

At 704, method 700 includes inputting the new ultrasound image sequence data into the trained artifact reduction network. The new ultrasound image sequence data may be inputted into the trained artifact reduction network in a manner similar to that described above in reference to method 600.

At 706, at 700 includes displaying an artifact-reduced version of the new ultrasound image sequence outputted by the artifact reduction network on a display device of the image processing system (e.g., display device 234). In preferred embodiments, the artifact-reduced image sequence may be displayed on the display device in real time, meaning as an examiner manipulates an ultrasound probe of the image processing system on a body of a subject of an examination. In some embodiments, the artifact-reduced image sequence may be displayed along with (e.g., alongside) a corresponding noisy image inputted into the artifact reduction network. For example, the input image and the artifact-reduced image may both be displayed side by side on a single monitor, or using a plurality of monitors. Additionally or alternatively, the artifact-reduced image sequence may be stored in a storage device of the image processing system (e.g., image database 214), or a different storage device.

FIG. 8 shows an exemplary artifact-reduced image 804 outputted by the trained artifact reduction network, where an amount of haze in an input image 802 has been removed. Structural elements of input image 802, such as a wall 806 of a heart, are more clearly distinguished from non-structural elements, such as a cavity 808. Artifact-reduced image 804 may have a lesser amount of haze than an artifact-reduced image outputted by a CNN trained on simulated data, or an image produced by a different method for reducing clutter artifacts. By reducing an amount of clutter artifacts in the original, higher-clutter ultrasound image, an accuracy of a diagnosis made by an examiner may be increased, and a number of examinations performed on a subject of the higher-clutter ultrasound image may be reduced, thereby reducing both imaging costs and a burden on the subject.

The technical effect of training a clutter artifact-reduction deep learning neural network on training data generated from sequences of ultrasound images acquired from a subject, the training data including target images with low, naturally occurring amounts of clutter, and input images including naturally occurring clutter added via artifact overlays, is that an amount of clutter artifacts removed from an ultrasound image by the neural network may be increased.

The disclosure also provides support for a method for an image processing system, comprising: receiving a sequence of medical images including an amount of clutter artifacts, reducing the amount of clutter artifacts present in the sequence of medical images using a trained data-driven model, the data-driven model trained on image sequence pairs including a first, lower-clutter image sequence as a target image sequence, and a second, higher-clutter image sequence as an input image sequence, the higher-clutter image sequence generated by superimposing an artifact overlay on the lower-clutter image sequence, the lower-clutter image sequence generated by an imaging device during a medical exam of a subject, and displaying an artifact-reduced version of the sequence of medical images on a display device of the image processing system and/or storing the artifact-reduced version in a memory of the image processing system, the artifact-reduced version outputted by the data-driven model. In a first example of the method, the medical images include in-vivo echography ultrasound data from any stage of an image acquisition chain from generating a signal via a transducer element to displaying an image on the display device. In a second example of the method, optionally including the first example, the data-driven model is a spatio-temporal three dimensional deep convolutional neural network (CNN). In a third example of the method, optionally including one or both of the first and second examples, the artifact-reduced version is displayed on the display device in real time. In a fourth example of the method, optionally including one or more or each of the first through third examples, the artifact overlay comprises a collection of copies of one or more haze patches extracted from higher-clutter medical data of one or more higher-clutter image sequences, where a haze patch is a spatio-temporal three dimensional region within a higher-clutter medical image sequence including few or no structural elements of a subject of the higher-clutter medical image. In a fifth example of the method, optionally including one or more or each of the first through fourth examples, the method further comprises: stacking or positioning the copies of the one or more haze patches to minimize a space between the copies of the one or more haze patches. In a sixth example of the method, optionally including one or more or each of the first through fifth examples, the method further comprises: morphing and/or gain adjusting the artifact overlay and/or one or more copies of the one or more haze patches to increase a diversity of haze data of the one or more haze patches. In a seventh example of the method, optionally including one or more or each of the first through sixth examples, the method further comprises: applying a weighting mask to a haze patch of the one or more haze patches to eliminate structural elements of the haze patch from being included in the artifact overlay. In a eighth example of the method, optionally including one or more or each of the first through seventh examples, the method further comprises: applying a weighting mask to both the artifact-reduced version and the target image sequence prior to a calculation of a loss function during training of the data-driven model. In a ninth example of the method, optionally including one or more or each of the first through eighth examples, the images of the image sequence pairs are scan-converted from a beamspace domain prior to being inputted into the data-driven model. In a tenth example of the method, optionally including one or more or each of the first through ninth examples, image data of the image sequence pairs includes one of: complex demodulated in-phase/quadrature (IQ) channel data, beamformed IQ data, envelope data, log-compressed envelope data, and radio frequency (RF) data.

The disclosure also provides support for an image processing system comprising: a processor, and a non-transitory memory including instructions that when executed cause the processor to: input a sequence of ultrasound images including an amount of clutter artifacts into a trained data-driven model, the data-driven model trained on a plurality of training pairs of image sequences, each training pair including a first, ground truth ultrasound image sequence with a lower amount of clutter artifacts acquired from a subject during an examination, and a second ultrasound image sequence with a higher amount of clutter artifacts, the second ultrasound image sequence generated by superimposing the clutter artifacts on the first, ground truth ultrasound image sequence, and display an artifact-reduced version of the sequence of ultrasound images on a display device of the image processing system and/or storing the artifact-reduced version in a memory of the image processing system, the artifact-reduced version outputted by the data-driven model. In a first example of the system, the clutter artifacts are superimposed on the first ultrasound image sequence via an artifact overlay having the same dimensions as the first ultrasound image sequence, the artifact overlay created out of extracted portions of a third ultrasound image sequence including a higher amount of clutter artifacts, the extracted portions including few or no structural elements of a subject of the third ultrasound image sequence. In a second example of the system, optionally including the first example, a mask is applied to one of: one or more of the extracted portions to remove the structural elements from the extracted portions, and the artifact-reduced version and the first, ground truth ultrasound image sequence prior to a calculation of a loss function during training of the data-driven model. In a third example of the system, optionally including one or both of the first and second examples, the extracted portions within the artifact overlay are synchronized to cardiac events of the first ultrasound image sequence. In a fourth example of the system, optionally including one or more or each of the first through third examples, a first plurality of ultrasound images of the first, ground truth ultrasound image sequence and a second plurality of ultrasound images of the second ultrasound image sequence are inputted into the data-driven model during each iteration of training.

The disclosure also provides support for a method for an image processing system, comprising: receiving a sequence of medical images including an amount of clutter artifacts, reducing the amount of clutter artifacts present in the sequence of medical images using a trained data-driven model, the data-driven model trained on training data including pairs of lower-clutter target image sequences and higher-clutter input image sequences, and displaying an artifact-reduced version of the sequence of medical images on a display device of the image processing system, the artifact-reduced version outputted by the data-driven model, wherein training the data-driven model includes: receiving a plurality of sequences of medical images, manually classifying each sequence of the plurality of sequences based on an amount of clutter artifacts included in the medical images of the sequence, to generate a first set of sequences having an insignificant amount of clutter artifacts, and a second set of sequences having an excessive amount of clutter artifacts, selecting a first, lower-clutter image sequence of the first set of sequences, selecting one or more higher-clutter images from the second set of sequences, manually selecting one or more spatio-temporal three dimensional (3D) regions within the selected one or more higher-clutter images including clutter artifacts and few or no structural elements of an anatomical region of a subject of the one or more higher-clutter images, extracting portions of the one or more higher-clutter images corresponding to the one or more spatio-temporal 3D regions, generating a clutter artifact overlay for the first, lower-clutter image sequence based on the extracted portions, superimposing the clutter artifact overlay on the first, lower-clutter image sequence to generate a third, higher-clutter image sequence with a higher amount of clutter artifacts, generating a training pair of image sequences including the first, lower-clutter image sequence as a target image sequence and the third, higher-clutter image sequence as an input image sequence, and training the data-driven model on training data including the training pair. In a first example of the method, the medical images are ultrasound images. In a second example of the method, optionally including the first example, training the data-driven model on the training data including the training pair further comprises applying a mask to an extracted portion to eliminate a contribution of a structural element of an anatomical region visible within the a 3D region in a loss function used during training. In a third example of the method, optionally including one or both of the first and second examples, generating the clutter artifact overlay for the first, lower-clutter image sequence based on the extracted portions further comprises: adjusting one or more proportions of an extracted portion, creating copies of an adjusted portion, and positioning the copies in the artifact overlay to minimize a space between the copies.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method for an image processing system, comprising:
receiving a sequence of medical images including an amount of clutter artifacts;
reducing the amount of clutter artifacts present in the sequence of medical images using a trained data-driven model, the data-driven model trained on image sequence pairs including a first, lower-clutter image sequence as a target image sequence, and a second, higher-clutter image sequence as an input image sequence, the higher-clutter image sequence generated by superimposing an artifact overlay on ultrasound images of the lower-clutter image sequence, the lower-clutter image sequence generated by an imaging device during a medical exam of a subject; and
displaying an artifact-reduced version of the sequence of medical images on a display device of the image processing system and/or storing the artifact-reduced version in a memory of the image processing system, the artifact-reduced version outputted by the data-driven model;
wherein the artifact overlay includes a plurality of haze patches positioned to cover a respective ultrasound image of the first, lower-clutter image sequence while minimizing a space between each haze patch, the haze patches extracted from cavities in ultrasound images of the higher-clutter image sequence.

2. The method of claim 1, wherein the medical images include in-vivo echography ultrasound data from any stage of an image acquisition chain from generating a signal via a transducer element to displaying an image on the display device.

3. The method of claim 1, wherein the data-driven model is a spatio-temporal three dimensional deep convolutional neural network (CNN).

4. The method of claim 3, wherein the artifact-reduced version is displayed on the display device in real time.

5. The method of claim 1, wherein each haze patch of the plurality of haze patches is a spatio-temporal three dimensional region within a higher-clutter medical image sequence that includes few or no anatomical structures of a subject of the higher-clutter medical image.

6. The method of claim 5, further comprising stacking the copies of the one or more haze patches to minimize a space between the copies of the one or more haze patches.

7. The method of claim 5, further comprising morphing and/or gain adjusting the artifact overlay and/or one or more copies of the one or more haze patches to increase a diversity of haze data of the one or more haze patches.

8. The method of claim 5, further comprising applying a weighting mask to a haze patch of the one or more haze patches to eliminate structural elements of the haze patch from being included in the artifact overlay.

9. The method of claim 5, further comprising applying a weighting mask to both the artifact-reduced version and the target image sequence prior to a calculation of a loss function during training of the data-driven model.

10. The method of claim 1, wherein the images of the image sequence pairs are scan-converted from a beamspace domain prior to being inputted into the data-driven model.

11. The method of claim 1, wherein image data of the image sequence pairs includes one of:

complex demodulated in-phase/quadrature (IQ) channel data;
  beamformed IQ data;
  envelope data;
  log-compressed envelope data; and
  radio frequency (RF) data.

12. An image processing system comprising:

a processor, and a non-transitory memory including instructions that when executed cause the processor to:
    input a sequence of ultrasound images including an amount of clutter artifacts into a trained data-driven model, the data-driven model trained on a plurality of training pairs of image sequences, each training pair including a first, ground truth ultrasound image sequence with a lower amount of clutter artifacts acquired from a subject during an examination, and a second ultrasound image sequence with a higher amount of clutter artifacts, the second ultrasound image sequence generated by superimposing the clutter artifacts on the first, ground truth ultrasound image sequence; and
  display an artifact-reduced version of the sequence of ultrasound images on a display device of the image processing system and/or storing the artifact-reduced version in a memory of the image processing system, the artifact-reduced version outputted by the data-driven model;
  wherein the superimposed clutter artifacts of the second ultrasound image sequence further comprise a plurality of haze patches positioned to cover a respective ultrasound image of the first, ground truth ultrasound image sequence while minimizing a space between each haze patch, the haze patches extracted from cavities in ultrasound images of a third ultrasound image sequence including a higher amount of clutter artifacts.

13. The image processing system of claim 12, wherein the clutter artifacts are superimposed on the first ultrasound image sequence via an artifact overlay having the same dimensions as the first ultrasound image sequence, the artifact overlay created out of extracted portions of the third ultrasound image sequence, the extracted portions including few or no structural elements of a subject of the third ultrasound image sequence.

14. The image processing system of claim 13, wherein a mask is applied to one of:

one or more of the extracted portions to remove the structural elements from the extracted portions; and
  the artifact-reduced version and the first, ground truth ultrasound image sequence prior to a calculation of a loss function during training of the data-driven model.

15. The image processing system of claim 13, wherein the extracted portions within the artifact overlay are synchronized to cardiac events of the first ultrasound image sequence.

16. The image processing system of claim 12, wherein a first plurality of ultrasound images of the first, ground truth ultrasound image sequence and a second plurality of ultrasound images of the second ultrasound image sequence are inputted into the data-driven model during each iteration of training.

17. The method of claim 1, wherein the haze patch is extracted from a hypoechoic region of an ultrasound image.

18. The method of claim 1, wherein the haze patch is defined by a bounding box, and the bounding box is maintained at a same location over a plurality of frames of the sequence, such that a haze patch is extracted from each frame of the plurality of frames at the same location.

\* \* \* \* \*